United States Patent [19]

Sloan

[11] 4,221,225

[45] Sep. 9, 1980

[54] BODY CAVITY EXAMINATION DEVICE

[76] Inventor: Noah H. Sloan, 594 Linden, Elmhurst, Ill. 60126

[21] Appl. No.: 959,470

[22] Filed: Nov. 13, 1978

[51] Int. Cl.³ .............................................. A61B 10/00
[52] U.S. Cl. ................................. 128/750; 73/425.6; 128/278
[58] Field of Search ...................... 128/750, 278, 276; 73/425.6

[56] References Cited

U.S. PATENT DOCUMENTS

| | | | |
|---|---|---|---|
| 3,285,296 | 11/1966 | Ishimaru et al. | 73/425.6 |
| 3,398,743 | 8/1968 | Shalit | 128/278 |
| 3,735,751 | 5/1973 | Katz | 128/750 |
| 3,855,997 | 12/1974 | Sauer | 128/276 X |
| 3,863,624 | 2/1975 | Gram | 128/276 X |
| 3,889,657 | 6/1975 | Baumgarten | 128/276 X |
| 3,889,682 | 6/1975 | Denis et al. | 128/276 X |
| 3,892,226 | 7/1975 | Rosen | 128/750 |
| 3,946,739 | 3/1976 | Berman et al. | 128/276 X |

*Primary Examiner*—Kyle L. Howell

*Attorney, Agent, or Firm*—Dressler, Goldsmith, Shore, Sutker & Milnamow, Ltd.

[57] ABSTRACT

A body cavity examination device is provided for introducing fluid through a body cavity and then withdrawing the fluid for examination, while selectively determining which particulate matter from the body cavity is ultimately collected for examination. The device includes a hollow member. One end of the hollow member is a fluid conduit which is insertable into the body cavity. The container which holds the fluid that is introduced through the body cavity is in fluid communication with the member. A collection receptacle is releasably secured to the opposite end of the member and is positionable in fluid communication with the member. A filter member is positioned in the opening such that all fluid withdrawn from the body cavity passes through the filter which collects particulate matter greater than a predetermined size. The fluid is introduced into the body cavity from the container and is withdrawn from the body cavity, whereupon the fluid passes through the filter member.

9 Claims, 4 Drawing Figures

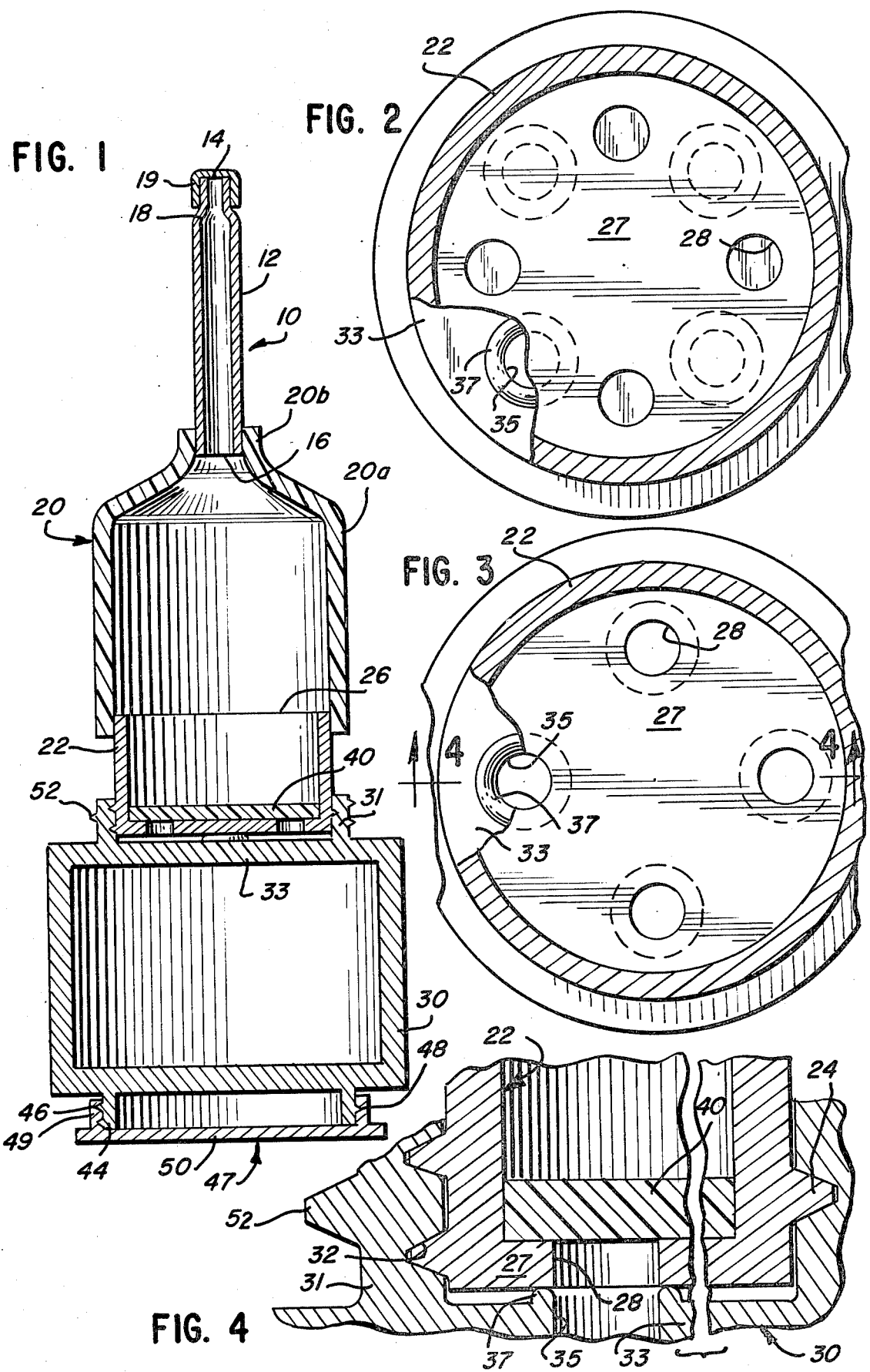

BODY CAVITY EXAMINATION DEVICE

BACKGROUND OF THE INVENTION

The present invention pertains to a device and a method for flushing a body cavity with a wash solution, and withdrawing the solution along with particulate matter from the body cavity so that the particulate matter can be examined.

Numerous prior art devices are known for flushing body cavities. U.S. Pat. No. 3,892,226 to Rosen, for example, discloses a urinary bladder irrigation-evacuator for introducing a fluid into a urinary bladder and thereafter withdrawing the fluid and particulate matter. The particulate matter is deposited in a collecting receptacle while the fluid is filtered and recirculated to the bladder. With the Rosen device, all particulate matter which is deposited is collected in the receptacle. This is disadvantageous where there are relatively great quantities of particulate matter in the body cavity, as when the gastro-intestinal tract is being examined. In such instances, the large amounts of undesired particulate matter, such as stool, make it more difficult upon examination of the particulate matter to locate and examine the body tissue which is collected. Where the larger particulate matter is stool, it can also contaminate the tissue cells which are to be examined.

SUMMARY OF THE INVENTION

The examination device of the present invention is used to alternately introduce fluid into a body cavity and then withdraw the fluid together with pieces of particulate matter from the body cavity for examination, while selectively determining which particulate matter is ultimately collected for examination.

The device includes a hollow member having an opening extending therethrough. One end of the hollow member is an open end portion adapted for positioning within the body cavity. A pump member is in fluid communication with the hollow member for introducing fluid into the body cavity through the hollow member and for withdrawing the fluid, together with pieces of particulate matter from the body cavity suspended in the fluid, from the body cavity into the hollow member. A collection receptacle is in fluid communication with the pump member and is selectively removable from the remainder of the body cavity examination device. A filter member is positioned between the open end portion of the hollow member and the receptacle and provides fluid communication between the hollow member and the receptacle.

In accordance with this invention, the fluid and particulate matter withdrawn from the body cavity pass through the hollow member and then through the filter member and into the receptacle. The filter member collects the larger pieces of suspended particulate matter while permitting smaller pieces of particulate matter suspended in the fluid to enter the receptacle.

In the preferred embodiment, the pump member is a manually compressible bulb which is positioned between the hollow member and the receptacle, and the fluid withdrawn from the body cavity travels through the hollow member, the bulb and then the filter before entering the receptacle. The fluid is introduced into the body cavity by squeezing the bulb, and the fluid is withdrawn from the body cavity by the suction forces created by the tendency of the squeezed bulb to return to its original unsqueezed and undeformed condition. The filter is positioned in a conduit segment between the bulb and the receptacle.

A method of collecting cellular material from a body cavity for examination in accordance with the present invention includes the steps of inserting a fluid conduit into the body cavity, introducing a fluid into the body cavity through the fluid conduit, withdrawing the fluid from the body cavity, passing the fluid through a filter which collects the larger pieces of particulate matter suspended in the fluid while permitting smaller pieces of particulate matter suspended in the fluid to pass through the filter, collecting the smaller pieces of particulate matter and fluid in a fixative solution, and separating the smaller pieces of particulate matter from the fluid and the fixative solution for examination.

BRIEF DESCRIPTION OF THE DRAWING

FIG. 1 is a cross-sectional view of the examination device of the present invention;

FIG. 2 is a plan view of the bottom wall of the hollow member, partially broken away, and the top wall of the receptacle in a first position;

FIG. 3 is a plan view of the bottom wall of the hollow member, partially broken away, and the top wall of the receptacle in a second position; and FIG. 4 is a cross-sectional view taken along line 4—4 in FIG. 3.

DETAILED DESCRIPTION OF THE PREFERRED EMBODIMENT

The present invention relates to an examination device for obtaining cells from a body cavity for examination. Although the present invention is adapted for use with many body cavities, such as the vagina or uterus, it is particularly suitable for use in examining the gastro-intestinal tract. However, it should be noted that the scope of the invention is not limited to the specific body cavities discussed herein.

The examination device includes a hollow member 12 which forms a fluid conduit having open ends 14 and 16. The fluid conduit is adapted for insertion into a body cavity and may include a lubricated tip 18 to facilitate insertion into the body cavity. The tip 18 is initially covered by a removable cap 19 to protect the lubricant. The cap is snugly secured to the tip as by a frictional fit.

The device 10 further includes a container 20 which initially holds the fluid which is introduced into the body cavity. In the illustrated embodiment, the container 20 is a deformable, squeezable bulb which has a large diameter central and lower portion 20a and narrower diameter upper end portion 20b. Upper end portion 20b has an inner diameter approximately equal to the outer diameter of the hollow member 12 to which it is secured above open end 16, and lower end portion 20a has an inner diameter approximately equal to the outer diameter of the end of hollow conduit segment 22 to which it is secured. The securement of the container 20 to the hollow member 12 and conduit segment 22 is by any suitable means, such as by a friction fit. The squeeze bulb is airtight and is in fluid communication with both the hollow member 12 and conduit segment 22.

A receptacle 30 is releasably secured to the opposite, bottom end of the conduit segment 22, and is in fluid communication with the conduit segment. As shown in FIG. 1, the receptacle is positioned below the conduit segment 22 to which it is detachably connected. The receptacle contains a fixative solution which is described in greater detail hereinbelow.

The conduit segment 22 and the receptacle 30 are provided with means for releasably securing the receptacle to the conduit segment. As shown in FIG. 4, the releasable securement means comprises a continuous helical tooth 24 projecting outwardly from the outer surface of the sidewall of the bottom portion of the conduit segment 22, and a corresponding continuous helical groove 32 defined by the inside wall of the neck portion 31 of the receptacle 30. With the foregoing arrangement, the receptacle 30 can be rotated counter-clockwise to screw the receptacle on to the conduit segment 22; when the receptacle is positioned on the conduit segment 22, the receptacle can be turned clockwise to remove the receptacle from the conduit segment.

The conduit segment 22 has an open end 26 and a bottom wall 27 at the opposite end that defines at least one, and preferably a plurality, of through apertures 28. The receptacle 30 has a top wall 33 that defines at least one, and preferably a plurality, of through apertures 35. One of the aforesaid pluralities of apertures, such as apertures 35, has an elastomeric ring 37 surrounding each aperture and projecting outwardly from the upper surface of the top wall 33. The elastomeric rings 37 are secured to the upper surface of top wall 33 and form a fluid-tight seal with the lower surface of the bottom wall 27 of the conduit segment 22. Accordingly, once the receptacle 30 is received on the conduit segment 22, the receptacle is movable between two positions. In the first position, shown in FIG. 2, the apertures 35 are not in registry with the apertures 28 and the elastomeric rings 37 are in sealing engagement with the bottom wall 27 to prevent fluid from passing from the conduit segment to the receptacle. This position is desired until after the squeeze bulb is squeezed to introduce the fluid into the body cavity.

After the fluid is introduced into the body cavity, it is desired to have the fluid enter the receptacle. To accomplish this, the receptacle is rotated relative to the conduit segment until the apertures 28 are in registry with the apertures 35; in this position, which is depicted in FIG. 3, the receptacle 30 is in fluid communication with the conduit segment 22.

Of course, other means may be used to provide selective communication between the receptacle and the remainder of the device in accordance the the present invention. For example, the entire area defined by the neck portion 31 of the receptacle can define an opening which communicates with a corresponding opening defined by the entire area within the inside surface of the conduit segment 22. A flat member can be initially positioned in sealing engagement with the entire area of the opening to prevent communication between the receptacle and the remainder of the device, and the flat member can be removed when desired to provide communication between the receptacle and the conduit segment.

In accordance with a further feature of the present invention, a filter member 40 (FIGS. 1 and 4) is provided to collect relatively large pieces of particulate matter and thereby prevent the relatively large pieces of particulate matter from entering the receptacle 30. The filter is particularly desirable when the body cavity is the rectum, so that the filter can collect the stool which is not useful for examination purposes while permitting smaller cellular materials which are desired for examination to enter the receptacle. The filter 30 is positioned in the conduit segment 22 and is supported by the upper surface of the bottom wall 27.

The device 10 further includes means for securely closing the opening in the receptacle 30 after drainage of the wash solution into the receptacle is completed, so that the receptacle can be transported to a laboratory for testing. In the illustrated embodiment, this purpose is accomplished by providing a flange 44 (FIG. 1) that extends downwardly from the bottom wall of the receptacle 30. The flange 44 has a continuous helical tooth 46 on the outside surface of the flange. A cover member 47 is releasably secured to the flange 44 and has a continuous helical groove 48 on the inside surface of a vertical flange 49. The cover member also has a flat horizontal wall 50 that forms the base of the device.

The cover member 47 is secured to the flange 44 by rotating the cover member relative to the flange in a first direction, and is removable from the flange by rotating the cover member relative to the flange in the opposite direction. Before the device 10 is used and while it is being used, the cover member 47 preferably is secured to the flange 44.

After the wash solution is collected in the receptacle 30, the receptacle is removed from the remainder of the device by unscrewing the receptacle from the conduit segment 22. The cover member 47 is thereupon unscrewed from the flange 44, and is screwed on to the neck 31 of the receptacle. This is performed by rotating the cover member 47 relative to the receptacle, so that the groove 46 receives the continuous helical tooth 52 that is provided on the outer surface of the neck portion 31 of the receptacle. In the laboratory, the cover member is removable from the receptacle by rotating the cover member in the opposite direction relative to the receptacle.

The cover member sealingly engages the receptacle. The covered receptacle could even be sent by mail to a laboratory for examination.

The examination device would be used to examine the gastro-intestinal tract, for example, for cancerous cells, as follows. Since it is desired to obtain a specimen for examination that is as free as possible from contaminants of the digestive products of the lower intestinal tract, the patient would be on a low residue diet for one day prior to the examination, and the patient would be given an enema before the examination to remove as much of the stool content as possible from the rectum.

Initially, the squeeze bulb is filled with a wash solution and the receptacle contains a fixative solution. The fixative solution is about 90% ethyl alcohol by weight and is an isotonic solution for preserving and fixing the cells from the body cavity that are received in the fixative solution. The receptacle is oriented relative to the conduit segment such that there is no fluid communication therebetween.

The cap 19 is removed, and the hollow member 12 is then inserted into the body until the tip 18 is positioned in the rectum. The wash solution in the container 20 is forced into the rectum by gently squeezing the bulb. Loose tissue, cells and stool become suspended in the wash solution fluid.

The wash solution fluid and the particulate matter dispersed in the fluid are then withdrawn from the body cavity by releasing the squeeze bulb. The bulb thereby functions as an aspirator due to the suction which results from the tendency of the squeeze bulb to return to its undeformed configuration. The fluid and particulate matter are thus drawn back into the container 20 through the opening 14 and the hollow member 12.

The receptacle 30 is then rotated relative to the conduit segment 22 until the apertures 28 and 35 are aligned so that the receptacle is in fluid communication with the conduit segment. Since the receptacle 30 is positioned below the conduit segment 22, gravity causes the fluid to pass from the container 20 into the conduit segment 22 and through the filter 40 to the receptacle 30. The pores in the filter 40 are of a predetermined size which is larger than the diameter of cancer cells which are found in cancer of the rectum, and smaller than contaminants such as particles of stool. The examination device would remain standing while the fluid drains through the filter, which usually takes from about four hours to about six hours.

After the draining is completed, the collection receptacle 30 is detached from the examination device by rotating the receptacle relative to the conduit segment.

The cover member is removed from the bottom of the receptacle and is secured to the neck portion of the receptacle. The receptacle is taken to the laboratory, where the cover member is removed to provide access to the contents of the receptacle. The particulate matter is separated from the fixative solution as by placing the fixative solution in a centrifuge, and the sediment which contains the particulate matter is smeared on a slide and examined for the presence of cancer cells.

The device could likewise be used for vaginal Pap smears, although a lesser amount of wash solution would be required. With suitable instructions, a woman could use the device herself. The tip 18 of the device is inserted into the vagina while the woman is lying on her back with her knees elevated. The bulb 20 is squeezed to introduce the solution into the vagina. The women then stands, so that the wash solution reenters the device both due to the aspiration effect of the bulb and the force of gravity. Once the solution has drained into the receptacle 30, the receptcale is detached from the remainder of the device and covered by cover member 47. The sealed receptacle is then transported to a laboratory for examination purposes.

The above detailed description of this invention has been given for ease of understanding only. No unnecessary limitations should be understood therefrom, as modifications will be obvious to one skilled in the art.

What is claimed is:

1. A body cavity examination device for alternately introducing fluid into a body cavity and then withdrawing the fluid and pieces of particulate matter suspended therein for examination, comprising:
   a hollow member having a single opening extending therethrough, one end of said member comprising an open end portion adapted for positioning within the body cavity;
   pump means in fluid communication with said hollow member for introducing said fluid into said body cavity through said hollow member and for withdrawing said fluid, with said pieces of particulate matter from the body cavity suspended therein, from said body cavity into said hollow member, said pump means having a first end secured to the opposite end of said hollow member;
   a receptacle in fluid communication with said pump means;
   means for sealingly engaging said receptacle to said pump means and providing selective removability of said receptacle from the remainder of said body cavity examination device; and
   filter means positioned between said open end portion and said receptacle such that all fluid received in said receptacle passes through said filter means, said filter means providing fluid communication between said hollow member and said receptacle, whereby said fluid is introduced into said body cavity by said pump means and is withdrawn from said body cavity at least in part by said pump means, and said fluid when withdrawn from said body cavity passes through said hollow member and then through said filter means into said receptacle, and said filter means selectively determines the size of the particulate matter that is received in the receptacle by collecting the larger pieces of particulate matter suspended in said fluid while permitting smaller pieces of particulate matter suspended therein to enter said receptacle.

2. A device as defined in claim 1 wherein said pump means is a compressible bulb for initially containing said fluid, said bulb being manually compressible to introduce said fluid into said body cavity; and wherein said fluid is withdrawn from said body cavity by the suction forces created by the release of said manual compressive forces on said compressible bulb.

3. A device as defined in claim 1 wherein said receptacle is positioned beneath said hollow member so that said fluid when withdrawn from said body cavity passes through said filter means by the force of gravity.

4. A device as defined in claim 1 wherein a fixative solution is provided in said receptacle, said fixative solution containing about 90% ethyl alcohol by weight.

5. A device as defined in claim 1 further including a conduit segment having an opening extending therethrough, said conduit segment having one end secured to a first end of said pump means and an opposite end releasably secured to said receptacle, said pump means having an opposite end secured to the end of said hollow member opposite said open end portion.

6. A device as defined in claim 5 wherein said conduit segment has a continuous helical tooth projecting outwardly from the outer surface thereof and said receptacle has a continuous helical groove corresponding in diameter to said tooth, whereby said receptacle is receivable on said conduit segment and detachable from said conduit segment by rotating said receptacle relative to said conduit segment.

7. A device as defined in claim 5 wherein said conduit segment has a bottom wall which defines at least one first aperture, and said receptacle has a top wall which defines at least one second aperture, means sealingly engaging said top wall and said bottom wall when said receptacle and said conduit segment are in a first orientation in which said first aperture is offset from said second aperture so that said fluid is prevented from entering said receptacle, and said receptacle being rotatable relative to said conduit segment to a second position in which said first aperture and said second aperture are in registry so that said receptacle is in fluid communication with said conduit segment.

8. A device for alternately introducing fluid into a body cavity and then withdrawing the fluid and particulate matter suspended therein for examination comprising:
   a hollow member having an opening extending therethrough, one end of said hollow member comprising a fluid conduit having an open end adapted for positioning within the body cavity;

a manually compressible bulb which is in fluid communication with said hollow member for introducing said fluid into said body cavity through said hollow member and for withdrawing said fluid, with said pieces of particulate matter from the body cavity suspended therein, from said body cavity into said hollow member, said bulb having a first end secured to the opposite end of said hollow member;

a conduit segment having an opening extending therethrough, said conduit having one end secured to a second end of said bulb;

a receptacle which is releasably secured to the opposite end of said conduit segment and is disposed below said conduit means and is positionable in fluid communication with said conduit segment, said conduit segment having a bottom wall which defines at least one first aperture, and said receptacle having a top wall which defines at least one second aperture;

means sealingly engaging said top wall and said bottom wall; and filter means positioned between said open end of said fluid conduit and said receptacle, whereby said fluid is introduced into said body cavity by compressing said bulb and is withdrawn from said body cavity together with pieces of particulate matter from said body cavity by the suction forces resulting from the release of said bulb, and said receptacle is movable between a first position in which said first aperture is offset from said second aperture so that said fluid is prevented from entering said receptacle, and a second position in which said first and second apertures are in registry so that said receptacle is in fluid communication with said conduit segment, bulb and hollow member for collecting said fluid and said filter means selectively determines the size of the particulate matter that is received in said receptacle.

9. A device for alternately introducing fluid into a body cavity and then withdrawing the fluid and particulate matter suspended therein for examination comprising:

a hollow member having an opening extending therethrough, one end of said hollow member comprising a fluid conduit having an open end adapted for positioning within the body cavity;

pump means in fluid communication with said hollow member for introducing said fluid into said body cavity through said hollow member and for withdrawing said fluid, with said pieces of particulate matter from the body cavity suspended therein, from said body cavity into said hollow member, said pump means having a first end secured to the opposite end of said hollow member;

a conduit segment having an opening extending therethrough, said conduit having one end secured to a second end of said pump means;

a receptacle which is releasably secured to the opposite end of said conduit segment and is disposed below said conduit means and is positionable in fluid communication with said conduit segment, said conduit segment having a bottom wall which defines at least one first aperture, and said receptacle having a top wall which defines at least one second aperture;

means sealingly engaging said top wall and said bottom wall; and filter means positioned between said open end of said fluid conduit and said receptacle, whereby said fluid is introduced into said body cavity by said pump means and is withdrawn from said body cavity together with pieces of particulate matter from said body cavity at least in part by said pump means, and said receptacle is movable between a first position in which said first aperture is offset from said second aperture so that said fluid is prevented from entering said receptacle, and a second position in which said first and second apertures are in registry so that said receptacle is in fluid communication with said conduit segment, said pump means and said hollow member for collecting said fluid and said filter means selectively determines the size of the particulate matter that is received in said receptacle.

* * * * *